United States Patent [19]
Holmes

[11] 4,143,656
[45] Mar. 13, 1979

[54] INSTRUMENT AND METHOD FOR INSERTING AN INTRAUTERINE CONTRACEPTIVE DEVICE

[75] Inventor: Gordon W. Holmes, Mississauga, Canada

[73] Assignee: Ortho Pharmaceutical Corporation, Raritan, N.J.

[21] Appl. No.: 894,312

[22] Filed: Apr. 7, 1978

Related U.S. Application Data

[63] Continuation of Ser. No. 781,592, Mar. 28, 1977, abandoned.

[51] Int. Cl.² ............................................. A61F 5/46
[52] U.S. Cl. ................................... 128/130; 206/438
[58] Field of Search ...................... 128/130, 260, 263; 206/438

[56] References Cited
U.S. PATENT DOCUMENTS

| | | | |
|---|---|---|---|
| 3,467,088 | 9/1969 | Robinson | 128/130 |
| 3,477,430 | 11/1969 | Barnhill | 128/130 |
| 3,515,132 | 6/1970 | McKnight | 128/130 |
| 3,516,403 | 6/1970 | Cournot | 128/263 X |
| 3,533,406 | 10/1970 | Tatum | 128/130 |
| 3,590,816 | 7/1971 | Rosenthal | 128/130 |
| 3,630,190 | 12/1971 | Baker | 128/130 |
| 3,635,215 | 1/1972 | Shea et al. | 128/130 |

*Primary Examiner*—Lawrence W. Trapp
*Attorney, Agent, or Firm*—Benjamin F. Lambert

[57] ABSTRACT

An instrument for inserting an intrauterine contraceptive device of the kind having one or more outwardly extending arms or protrusions is described. The insertion instrument comprising an inserter tube and coacting rod maintains the arm or arms of the device in an extended configuration during storage but quickly and facilely folds the arms of the device into a protective housing or sheath for insertion into the uterus and releases the device by a withdrawal of the protective housing. A uterine sound which may be employed with the insertion instrument is also described.

12 Claims, 13 Drawing Figures

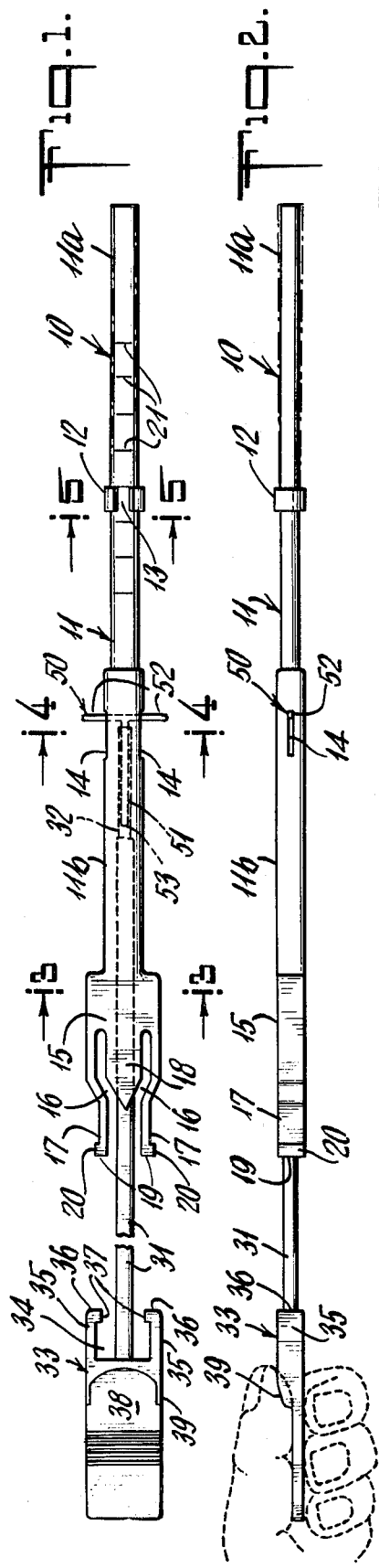
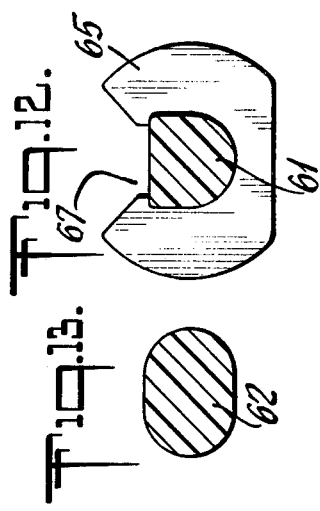
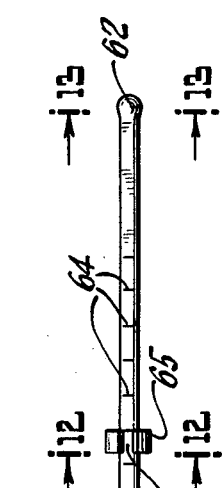
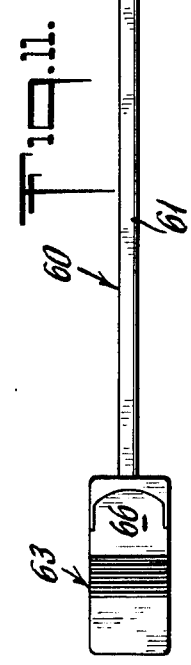
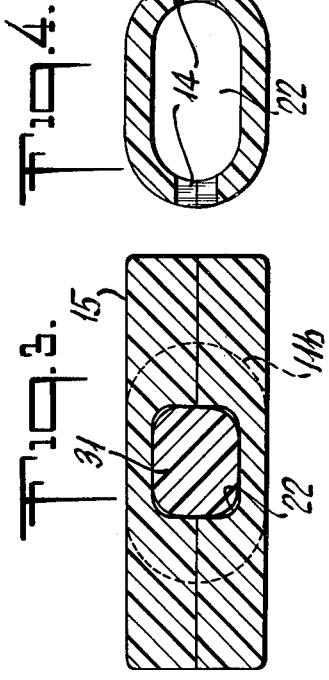
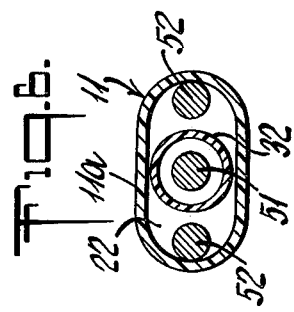
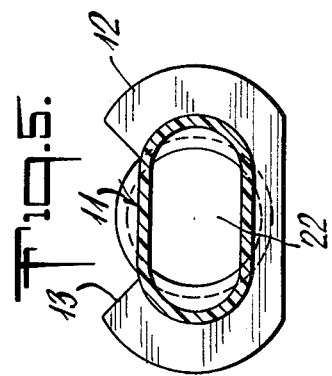

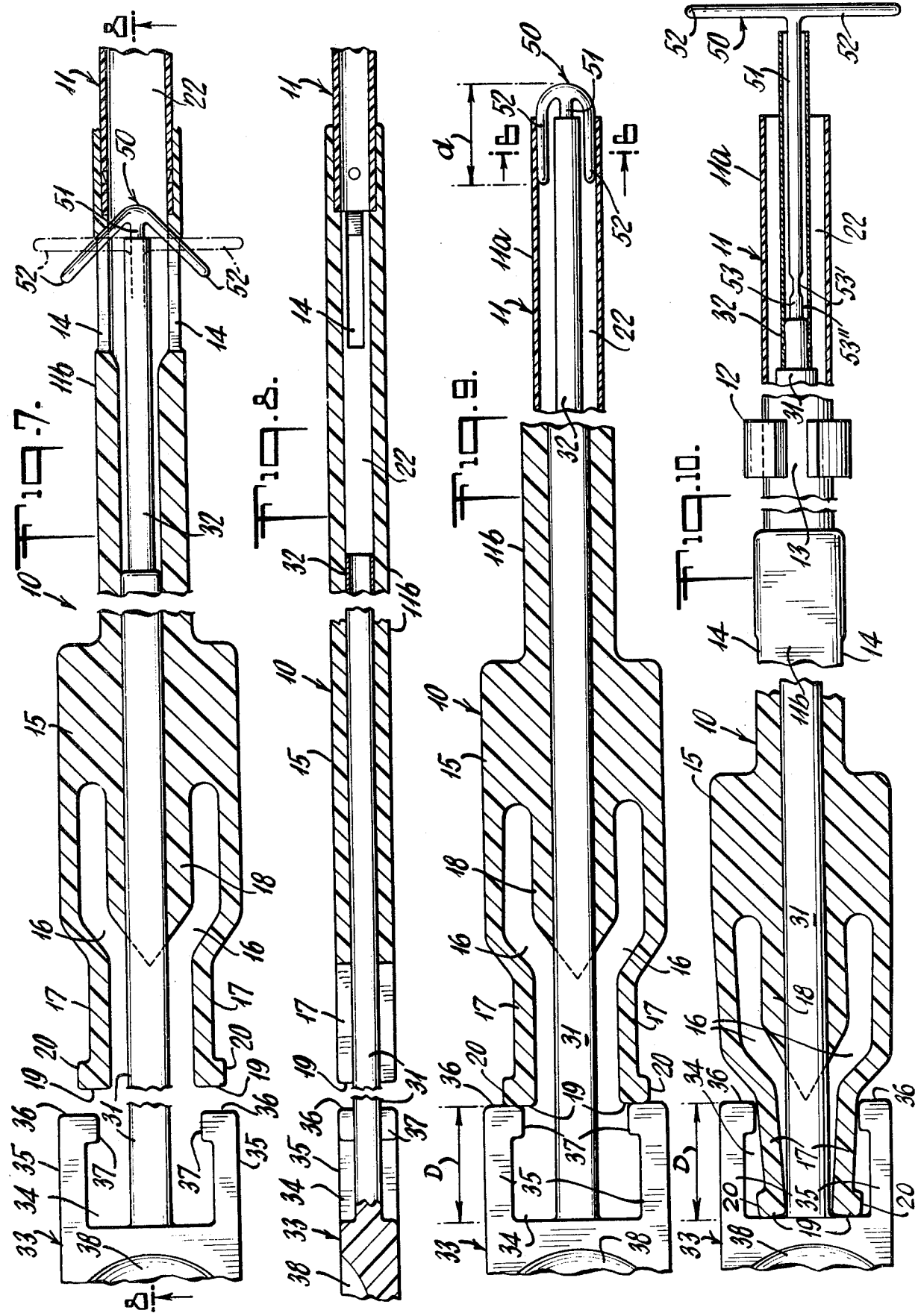

INSTRUMENT AND METHOD FOR INSERTING AN INTRAUTERINE CONTRACEPTIVE DEVICE

This is a continuation of application Ser. No. 781,592, filed Mar. 28, 1977, abandoned.

This invention relates to an instrument for inserting a sterile intrauterine contraceptive device into the uterine cavity; to a combination of contraceptive device and instrument for inserting same suitable for sterile packaging; and to methods for inserting contraceptive devices.

Intrauterine contraceptive devices, hereinafter sometimes referred to as IUDs are employed by insertion into the uterus when prevention of conception is desired. The use of such devices is based on the knowledge that the presence of a foreign object in the uterus discourages conception. The devices have been of various preformed configurations including a ring, a spiral, a bow, one which has a shape characteristic of a "7" and one which has a shape characteristic of a "T." The devices of various configurations are designed to occupy a significant portion of the space in the uterus and therefore are of effective dimensions which are larger than the cervical os through which they must pass. Thus, insertion of the IUD is carried out by use of an inserter which modifies the configuration of the IUD during insertion. It is contemplated that the IUD on release in the uterus assumes the original configuration. However, materials from which the devices are made generally have such properties that if any force is applied to the IUD for an extended time, the configuration assumed while the force has been applied is retained. When the IUD fails to assume its original configuration, its effectiveness is impaired. For this reason, it is undesirable to provide an insertion instrument in which the IUD is pre-positioned in an insertion configuration. Rather, the IUD is restrained into an insertion configuration for a brief few moments immediately prior to use thereby causing little or no distortion or impairment to the IUD.

Illustrative of this is a practice employed with one of the frequently employed IUDs which is in the shape of a "T". One method for inserting it employs an insertion tube and a complementary plunger. The tube is of sufficient size and malleability for retaining the extended arms of the device in a folded position during insertion and is released from this position by interaction with the plunger. Thus, when it is desired to insert the IUD, the physician at that time fits the extended arms of the "T" into the upper end of the insertion tube with his fingers while attempting to maintain sterile conditions. He then inserts the loaded tube through the cervical os into the uterine cavity and after locating the tube in the desired position pulls downward on the tube to expel the IUD while he attempts to maintain the IUD in the correct position in the uterus by holding the inner plunger stationary. When the insertion tube is withdrawn the arms of the "T" then unfold in the uterus.

This and other inserter instruments which require manual placement of the IUD in the inserter instrument by the physician are disadvantageous because it is cumbersome, time consuming, and further, increases the possibility of contamination and improper insertion. Moreover, where the IUD must be positioned by human manipulation, there exists an additional hazard of erroneous placement which may be a source of potential injury to the patient. Thus, for example, in the case of an IUD in the shape of a "T", the arms may be folded upward which could cause injury to the fundus on insertion of the unit itself or expulsion of the "T" from the insertion unit. With IUDs of certain configuration, the IUD may be positioned in the inserter by drawing back on the "tail," i.e., the string attached to the IUD for removal from the uterus. Such a method, however, is undesirable for an IUD having a "T" configuration since the arms would be drawn upwards. In some devices the folding of the IUD or placement in the inserter tube may be made to occur after the initial placement of the inserter in the uterus thereby providing less control. Generally most devices contemplate expulsion of the IUD from the inserter tube by interaction of the IUD with an inner plunger. If the plunger is pushed when the IUD is an place rather than being held stationary while retracting the inserter tube there could be serious injury to the fundus. The difficulty of controlling present devices sometimes leads to confusion for the physician and potential injury to the patient.

It is an object of the present invention to provide an improved insertion method and insertion instrument for an intrauterine contraceptive device having a stem with substantially transverse arms distally adjacent to and integral with the stem which can be employed without the need for dilation of the cervix.

It is another object of the present invention to provide a means for rapidly and facilely folding an intrauterine device having substantially transverse arms into a compact configuration in an insertion instrument in which the folding can be carried out immediately prior to insertion into the uterus thereby avoiding distortion of the intrauterine device caused by long-term prefolding.

A further object of this invention is to provide an integral mechanism which guards against automatic expulsion of the intrauterine device through the end of the insertion tube during the step of folding the transverse arms of the device and moving it into position.

Another object is to provide an insertion instrument in which the intrauterine device can be precisely positioned with its contoured folded tip slightly protruding beyond the end of the insertion tube of facilitate insertion through the cervical os.

An additional object is to provide an instrument which more precisely releases and positions the intrauterine device in the uterus to reduce to a minimum possible injury to the uterine wall or fundus.

A further object is to provide an insertion instrument of a malleable nature which is adaptable to being curved or bent to conform to the natural intrauterine curvature providing a smoother and more comfortable entry into the uterine cavity.

A further object is to provide an insertion instrument which makes it possible to control the lateral orientation of the IUD in the uterine cavity.

Another object is to provide an instrument of enhanced tactile sensitivity for placement control.

An additional object of the present invention is to provide insertion system which minimizes handling of the portion of the instrument which will become intrauterine so that sterile conditions can be maintained.

A still further object is to provide an insertion instrument in combination with an intrauterine device said combination being adaptable to sterile packaging.

A further object is to provide an optional preferred embodiment in which a disposable sterile uterine sound of similar design to the insertion device is employed, said sound being provided with identical depth scale and indicator as provided on the insertion instrument.

In accordance with the present invention there is provided an insertion instrument assembly to be employed for inserting into the uterus without the necessity for cervical dilation of a flexible intrauterine contraceptive device of the kind having at least one, preferably two, substantially horizontaly extending arm which comprises (a) an inserter tube adaptable for protectively housing the intrauterine device with the arms folded adjacent to the stem in an axially aligned position and (b) a coacting rod telescopically positioned in the tube, said insertion instrument assembly having an insertion end adapted to be passed through the cervix and being further provided with means adapted to receive the intrauterine device, to fold the arms or protrusions of the device, to control the position of insertion into the uterus, and to release the device in the uterine cavity. In the preferred embodiment of the present invention, the instrument is utilized for inserting a flexible contraceptive device having two transverse arms distally extending from a stem, generally in the shape which may be described as a "T".

The inserter tube adapted to protectively house said intrauterine device with the arm or arms folded adjacent to the stem in an axially aligned position, has an insertion section of a flexible nature and a manipulative section of a non-flexible nature. The insertion section is the forward part of the tube which will become intrauterine in use and the manipulative section is that part which will remain extrauterine in use. The tube is provided with an externally mounted slidable stop means for engaging the cervical os which is located on the insertion section of the tube and is susceptible of being adjusted to a predetermined position for proper depth of insertion. On the manipulative section of the tube posteriorly of the stop means, are located a pair of diametrically opposed axially extending apertures. The apertures are adapted to receive the intrauterine device so that the stem extends axially within the tube and the arm or arms extend through the apertures. The tube is provided with a handle at the posterior end. The handle is an integral part of the manipulative section and has a passageway therethrough which is in communication with the lumen or bore of the tube. The handle is bifurcated with the stems extending in a posterior direction and terminating in a flange with a projecting edge. The cross-sectional configuration of the lumen of the tube in the flexible insertion section is circular but that in the rigid manipulative section is non-circular.

The coacting rod to be telescopically positioned in the inserter tube and slidable therein is of malleable material with a retentive memory and is provided with a tubular receptacle section at the insertion end adapted to support the stem of the intrauterine device and with a handle at the posterior end. The handle is bifurcated with stems extending in an anterior or forward direction and has flanges with edges projecting oppositely to the edges in the handle of the inserter tube. The flanges are further spatially opposed and abuttable with the flanges of the inserter tube handle. The rod has a non-circular cross-sectional configuration complementing the cross-sectional configuration of the lumen of the rigid portion of the inserter tube.

The stems of one of the bifurcated handles are compressible and when compressed are adapted to be received in the area between the stems of the other handle which is at least as deep as the distance occupied by the arm of the intrauterine device within the tube in insertion position as subsequently described. While the device may be made operable with either handle being the compressible handle (i.e., handle with compressible stems), it is preferred that the inserter tube be provided with the compressible handle. The reason for the preference is that since it is the rearward motion of the inserter tube that is intended to release the intrauterine device, a more safe operation is possible if the rod handle is held immobile.

The inserter tube and rod coact in a manner such that pulling rearwardly on the inserter tube handle until the flanges of the stems of the inserter tube and rod handles are abutting causes a folding of the arms of the IUD and moves it to the insertion position with the contoured tip and the folded arms minimally projecting from the sheath provided by the insertion end of the tube. The conformable non-circular cross-section of the rod and rigid portion of the inserter tube permits this to occur without twisting. The instrument in this position is employed for insertion in the uterus. Thereafter, on compressing the compressible stem of one of the handles and drawing it within the area between the stems of the other handle retracts the sheath from around the IUD and releases the intrauterine device at the insertion end. Following this, releasing the compression pressure on the stem causes the inwardly and outwardly projecting edges of the handle susceptible of interlocking for a unitary withdrawal of the tube and rod from the uterus.

The inserter tube is preferably of flexible material at the insertion section so that although circular in cross-section before loading with the intrauterine device, it assumes an oval shape when loaded and acting as a snug protective sheath or housing for the IUD. The tube at the manipulative end is of rigid material. Although the tube may be made oval at the insertion end by use of rigid material, the added bulk resulting from this alternative renders this less preferable.

In a preferred embodiment of the present invention the handle of the rod is provided with a digit placement area, a contoured tactile area on the proximal surface where a physician may place his thumb or finger, which provides the physician with a means for sensitively controlling the instrument as it is being inserted into the uterine cavity and which communicates to him the orientation of the device during and after insertion.

In another preferred embodiment of the present invention, the inserter tube is provided with graduations to be employed with the stop means for more exact positioning of the intrauterine device, particularly, when employed with a companion uterine sound. These embodiments are subsequently described.

The objects and advantages of this invention will be more readily apparent from the following description and accompanying drawings.

FIG. 1 is a schematic front plan view in combination of a "T" shaped intrauterine device and an insertion instrument assembly comprising an inserter tube and a coacting rod, and showing the protruding arms of the device as initially positioned in the instrument.

FIG. 2 is a side view of FIG. 1.

FIG. 3 is a view, in cross-section, along 3—3 of FIG. 1.

FIG. 4 is a view, in cross-section, along 4—4 of FIG. 1.

FIG. 5 is a view, partly in cross-section and partly in elevation, along 5—5 of FIG. 1.

FIG. 6 is a view, in cross-section, along 6—6 of FIG. 9.

FIG. 7 is an enlarged fragmentary cross-sectional view of the assembly showing the intrauterine device.

FIG. 8 is a view, in cross-section, along 8—8 of FIG. 7.

FIG. 9 is an enlarged fragmentary cross-sectional view similar to FIG. 7 but in moved position and showing the folded intrauterine device contained therein.

FIG. 10 is a similar enlarged fragmentary view in moved position showing the unfolded arms of the intrauterine device.

FIG. 11 is a view of a companion uterine sound.

FIG. 12 is an enlarged view partly in cross-section and partly in elevation, along 12—12 of FIG. 11.

FIG. 13 is an enlarged view, in cross-section, along 13—13 of FIG. 11.

Referring to the drawings, particularly, FIG. 1, 2, 7 and 8, it will be seen that the intrauterine device insertion instrument assembly 10 embodying the present invention comprises an inserter tube 11 and a coacting rod 31 telescopically positioned in the tube and having mounted therein an intrauterine device 50.

The inserter tube is of two sections, a forward flexible insertion section 11a and a rearward substantially rigid manipulative section 11b which will remain extrauterine during use. Located on the exterior of the flexible section of the inserter tube is a slidably adjustable stop means 12, adjustable to a position corresponding to the position to which it is desired to insert the mounted insertion instrument assembly into the uterine cavity. (A view along the axis showing the stop means surrounding the flexible insertion section of the tube is seen in FIG. 5.) Located on the manipulative section of the tube is a pair of diametrically opposed axially extending apertures 14 through which the intrauterine device is initially placed in the instrument. The tube is provided at the posterior end with a handle 15 to facilitate grasping and manipulating the instrument said handle being an integral part of the manipulative section and having a passageway therethrough communicating with the lumen or axial bore 22 of the tube as hereinafter described. As best seen in FIGS. 1 and 7, the handle is bifurcated, having compressible stems 17 extending in a posterior direction said stems bracketing an area 16 through which the coacting rod 31 passes to enter into the lumen 22 of the tube. Preferably an extension 18 of the tube protrudes into the area 16, providing additional guiding support for the rod. The stems 17 terminate in flanges 19 with outwardly projecting edges 20, said flanges adaptable for serving as abutment means (see FIG. 9) and as interlocking means (see FIG. 10).

The slidable stop means 12 is a disc surrounding the flexible section 11a of the inserter tube and is preferably provided with a slot 13 to prevent occlusion of graduations 21 (see FIG. 1) which are preferably imprinted or embossed on the insertion section. The graduations indicate the depth of the uterine cavity as measured from the tip of the folded intrauterine device in the loaded insertion instrument (i.e., instrument ready for insertion into the uterus) as seen in FIG. 9. The graduations 21 correspond to graduations 64 on a companion uterine sound 60 (see FIG. 11) which may be and preferably is employed with the insertion instrument assembly 10 of the present invention.

The location of the apertures 14 with respect to the top or insertion end of the tube and the flange face on the terminal part of the handle of the tube is important. The apertures are located so that the intrauterine device reaches the insertion or loaded position when the tube has been drawn backward until further movement is stopped (see FIG. 9) as will be hereinafter more fully described.

The cross-sectional view of the aperture area is seen in FIG. 4 and shows that the cross-sectional dimensions of the lumen 22 may be larger in the vicinity of the aperture than the passageway in the handle portion (FIG. 3) to facilitate initial mounting of the intrauterine device. (See also FIG. 7).

The flexible nature of the insertion section permits the tube, when subjected to pressure, as occurs on the loading of the intrauterine device to assume an elliptical or oval cross-sectional shape thereby providing a snug sheath or protective housing for the stem and folded arms for the intrauterine device. The oval cross-sectional configuration of the tube while housing the stem and arms of the intrauterine device is seen in FIG. 6. The stop means 12 preferably has an oval cross-sectional configuration of the loaded insertion instrument and the oval cross-sectional configuration assumed by the tube in the vicinity of the stop means is seen in FIG. 5. (The dashed lines in FIG. 5 shows the normal round cross-sectional configuration of the tube. The modification of the tube from round to oval may be seen also with the aid of the dot-dashed lines representing the normal round shape seen at the upper end of the tube in FIGS. 1 and 2.)

The cross-sectional configuration of the lumen 22 in the manipulative section of the tube as well as the cross-sectional configuration of the coacting rod is important. These portions of the insertion instrument assembly have a non circular cross-section, i.e., it has at least one substantially flat or flattened surface in the cross-sectional configurations. Conveniently the configurations may be flattened ellipse or a rectangle with rounded corners or semi-circular somewhat in a shape which may be described as "D". However, it may be a square, triangle, polygon or an irregular shape with a flattened side. The flat or flattened sections of the rod and tube are conformable with each other although they need not be identical in shape; the conformance prevents rotation of the rod after insertion in the uterus. This is important for aiding the physician to control the plane of the intrauterine device during insertion and placement in the uterus. It is most usefully accomplished by having the flat surface of the handle and rod coincide with or be parallel to the plane of the intrauterine device.

The tube extension 18 provides added support for the rod. Although it may be omitted, it is part of the preferred embodiment and when employed its length is not critical. It is convenient for the tube extension to have a shape somewhat like an arrow pointing downward as shown in the drawings as a guide to the physician indicating the direction in which the moving force should be applied for releasing the IUD.

The coacting rod 31 is preferably provided at the top or insertion end with a tubular receptacle section 32 (see FIGS. 1, 9 and 10), said tubular receptacle section being adaptable to receive the stem 51 of an intrauterine device. It is provided at the posterior end with a bifurcated handle 33 with the stems 35 extendig in an anterior direction and bracketing a cut out area 34 surrounding the point of attachment of the rod to the handle, said stem provided with flanges 36 with inwardly projecting edges 37 serving as complementary abutment means and interlocking means to the outwardly projecting edges 20 of the flanges 19 of inserter tube 11. Preferably, the handle is provided with a grooved digit placement area 38 (see FIGS. 1 and 2) for either the index finger or thumb of the physician.

Although the rod 31 may be employed without a tubular receptacle section 32 at the insertion end, it is desirable to provide such tubular support for at least a portion of the stem and preferably for a substantial portion of the stem. It has been found that the terminal portion 53 of the stem of the intrauterine device, which usually has a narrower area 53' (see FIG. 10) which is punctured to hold the end of the wire with which the device may be wound and which is further punctured near the very end 53" to hold the "tail" or withdrawal string, may collapse when subjected to pressure if not supported. The tubular receptacle section is preferably constructed by providing for a reduced section 31' of the rod to which a tubular receptacle section is mechanically attached.

As seen most clearly in FIG. 9, the flanges 19 of the inserter tube 11 and the flanges 36 of the rod 31 are of such dimensions so that when the inserter tube is drawn back without compression on the stems 17 of handle 15, the flanges are in abutting relationship. This mechanism stopping the backward motion of the inserter tube stops the forward motion of the intrauterine device and provides for the exact placement of the folded intrauterine device in the insertion position at the forward end of the insertion tube with the contoured tip of the intrauterine device and the folded arms minimally projecting from the insertion end and prevents accidental expulsion of the device through the end of the tube prior to its insertion in the patient.

Further, as seen in FIG. 10 when stems 17 of handle 15 of the inserter tube are compressed laterally and drawn downwardly it may become cradled in the cut out area 34 and the outwardly projecting edges 20 of flanges 19 and the inwardly projecting edges 37 of flanges 36 are in overlapping relationship adapted to provide for interlocking so that on withdrawal of the instrument, the tube 11 and the rod 31 may move as a unit in an interlocked position. The distance "D" (see FIGS. 9 and 10) between the forward abuttable face of flanges 36 of the rod handle and the bottom of the cut out area 34 of the handle is important. As seen in FIG. 9, it should be slightly greater than the distance "d" between the tip of the folded intrauterine device extending out of the inserter tube and the end of the folded arm of the intrauterine device in the tube.

The tube handle 15 and rod handle 33 preferably have flat surfaces at the proximal and remote sides which coincide with the plane of the intrauterine device and with the planes of the flat surface of the rod 31 and of the complementary flat surface in the lumen 22 of the inserter tube. The flat handle surfaces are best seen in FIG. 2. The flat handles make known to the physician the orientation of the IUD and facilitates the exercise of better control.

The digit placement area 38 is best understood when viewed from the side as seen in FIG. 2. It is provided on the surface of the rod handle and thus in the same plane as the intrauterine device. The digit placement area 38 is contoured and has a concaved forward wall 39 against which the highly sensitive tip of the physician's thumb or finger may be pressed during insertion, providing better control, increased tactile sensitivity, and improved safety during the very delicate procedure required in the proper insertion of the IUD. It may further be provided with non-slip grooves for better grasp.

Initially the intrauterine device 50 is mounted in the insertion instrument 10 with the arms 52 of the IUD 50 in the open or extended configuration and exposed as seen in FIG. 1. The mounting is carried out by inserting the IUD 50 through the apertures 14 in the inserter tube 11 and positioning the IUD so that the stem 51 extends along the length of the tube (see also FIG. 7), then sliding the coacting rod 31 upward or forward until the stem end of the IUD 50 is seated in the tubular receptacle section 32. (An enlarged view of the receptacle section 32 is seen in FIG. 10.) In this initial position, the arms 52 of the "T" or the outwardly extending portion of any IUD having transverse portions extending from a stem are in a static position with no forces which might cause malformation or distortion thereof. Preferably the IUD is premounted, i.e., placed in the insertion instrument during manufacture and the combination sterilized and packaged for shipment. The IUD may also be premounted at the site and presterilized and stored in this position, thus avoiding the need to handle the IUD at the time of use.

At the time of use, the physician takes the presterilized insertion instrument assembly 10 with the preloaded IUD 50 and proceeds in the following manner to prepare for insertion of the IUD into the patient: The intended position or depth of insertion is determined with a uterine sound and the correct depth is then indicated on the insertion tube with a slidable stop means 12. The uterine sound employed may be a standard uterine sound or a companion uterine sound similarly graduated and hereinafter described. Then the handle 33 of the rod 31 is grasped with one hand and the stems 17 of handle 15 of the inserter tube 11 are grasped with the other hand and the tube 11 is drawn rearwardly or downwardly toward the handle of the rod until the flanges 19 and 36 of the respective handles are in abutting relationship as seen in FIG. 9. As seen in FIG. 7, the downward motion of the inserter tube 11 causes the IUD 50 to be drawn upward in the tube forcing the arms 52 to fold therein. Continuation of this downward motion conveys the IUD through insertion section 11a of the inserter tube and to the end of the tube until no more than the rounded top of the IUD 50 and a portion of the folded arms 52 extend slightly beyond the end of the tube as seen in FIG. 9. When the IUD is in the folded position, the flexible tube assumes an elliptical form as seen in FIG. 6. At this point the loaded instrument may be curved by the physician to more closely conform to the natural curvature of the insertion path. The abutment of the flanges of the handles prevents inadvertent expulsion of the IUD while it is being folded in place. The insertion instrument with the protectively mounted IUD is then inserted in the uterus to the previously determined position, i.e., until the stop means 12 makes contact with the exterior of the cervical os. Then pressure is applied to the compressible stems 17 of the bifurcated handle 15 of the inserter tube 11 to remove it from the abutting position and the inserter tube is drawn backward or downward while the rod 31 is held stationary by the handle 33 until the inserter tube handle 15 is within the cut out area 34 of rod handle 33 as seen in FIG. 10 whereupon at the insertion end, the tube is retracted from the IUD 50 releasing the extensible arms 52 which flex outwardly within the uterus to its normal unfolded position. Thereafter, the insertion instrument assembly 10 is withdrawn from the uterus depositing the device which in its original configuration becomes engaged within the uterine walls to perform its contraceptive function. As seen in FIG. 10, the oppositely facing protruding edges 20 and 37 of flanges 19 and 36 are in interlocking relationship so that when the rod handle 33 is grasped with one hand and drawn backward, withdrawal of both the tube and rod may be accomplished. The rod handle in the cut out portion optionally may be provied with additional grooves at the bottom of the cut out area to further interlock the protruding edge 20 but is not considered necessary. Since the IUD is mounted initially in the same plane as the flat surface of the rod handle, the interlocking of said handle with the inserter tube handle serves to indicate the orientation of the device during and after insertion and to aid the physician in maintaining the desired alignment of the device within the uterus. Further, since the IUD is released by a withdrawal motion of the inserter tube 11 rather than a pushing motion of the rod 31, the forward direction sometimes resulting in injury to the fundus is avoided. While the instrument is particularly adaptable for a device having a shape of a "T", it may be utilized for any contraceptive device having an elongated body or stem and having at least one arm or other perpendicularly extending bar or protrusion which is adaptable to being folded along its stem.

The inserter tube 11 is preferably made in two separate part of two materials corresponding to the two sections. The insertion section 11a should be of flexible material and be sufficiently thin-walled to allow the shape to change from round to oval or elliptical as the tube is loaded to house the folded intrauterine device. The lower manipulative section 11b should be made of more rigid material for manipulative ease and to prevent the turning of the coacting rod 31 within the tube. The coacting rod 31 is preferably made of malleable biologically inert plastic material with a retentive memory. By "malleable" is meant that the material permits external forces to be applied to conform the material to the desired shape but is of sufficient strength to retain its structure when subjected to no external force or to relatively minor external force such as occurs during insertion. Thus, a physician may contour the IUD loaded insertion instrument in the region which will become intrauterine on insertion, (i.e., the insertion section of the tube and the rod) to provide a curvature conforming to the curvature of the uterine cavity. The manipulative section of the tube and the rod handle are also preferably made of the same malleable material but the greater dimensions of these portions of the instrument render them substantially rigid. When the insertion instrument is employed with the companion uterine sound hereinafter described, it may be bent to the same curvature indicated by the uterine sound during the initial sounding by the physician. Suitable malleable materials which may be employed include, for example, polymeric materials such as acrylonitrile-butadiene-styrene (ABS plastic), or a mixture of acrylonitrile-butadiene rubber and styrene-butadiene resin, or other thermoplastic materials with strong memory properties. The preferred flexible material is polyethylene, although polypropylene, acrylic terpolymer, etc. may be employed. Polyethylene is also the preferred material for the tubular receptacle section of the rod although a more rigid material may be employed for this purpose. It is recognized that the insertion tube may be provided with an oval shape at the insertion end but use of a flexible material at the insertion end renders this unnecessary.

Preferably, the instrument is employed with a companion uterine sound 60 illustrated in FIG. 11. The sound comprises rod 61 with a rounded tip 62 and a handle 63 for insertion and manipulation, said rod having graduations 64 imprinted thereon and further provided with a slidably movable stop means 65 for indicating the position of a cervical cs. The stop means has a slot 67 to prevent occlusion of the graduations. The tip of the sound 62, seen in cross-section in FIG. 13, is of substantially the same dimensions as the rounded tip of the folded intrauterine device. The handle 63 further has a digit placement area 66 corresponding to a similar digit placement area 38 in the handle of the rod. The graduations imprinted on the rod indicate the depth of the uterine cavity as measured from the tip of the rod. These graduations correspond to the graduation on the inserter tube indicating the depth of the uterine cavity as measured from the tip of the folded intrauterine device protruding from the insertion end of the inserter tube. The sound is made of the same material as the coacting rod 31 of the insertion instrument so that both may be bent in the same way to correspond to the patient's anatomical variations.

In use, the sound is employed in a conventional manner by inserting into the uterine cavity, bending in a direction according to the naturel curvature and slidably adjusting the stop means. The direction of curvature of the sound is observed and the insertion instrument is bent to conform to the observed curvature. The distance is read on the graduations of the sound and the stop means of the inserter tube is movably adjusted to the corresponding distance. The use of the companion uterine sound is advantageous in providing a more precise correspondence between the measured depth and the distance to be indicated on the instrument.

Having described the invention in specific detail and exemplified in the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. An insertion instrument for inserting into the uterus an intrauterine device having a stem and at least one substantially horizontally extending flexible arm comprising
    (a) an inserter tube adapted to protectively house said intrauterine device with the arm or arms folded adjacent to the stem in an axially aligned position, said tube having an insertion section of a flexible nature and an manipulative section of a non-flexible nature, said tube having (i) an externally mounted slidable stop means for engaging the cervical os, said stop means being located on the insertion section of the tube, said stop mean susceptible of adjustment to a predetermined position for insertion, (ii) a pair of diametrically opposed axially extending apertures located on the manipulative section of the tube posteriorly of the stop means, said apertures adapted to receive the intrauterine device so that the stem extends axially within the tube and the arm or arms extend through said apertures; and

11

(iii) a handle at the posterior end of the tube, said handle being an integral part of the manipulative section and having a passageway therethrough, said passageway in communication with the lumen of the tube and further being bifurcated with the stems and terminating in a flange with a projecting edge; and (b) a coacting rod of malleable material with a retentive memory in telescopic relationship to the inserter tube and slidable therein, said rod having (i) a tubular receptacle section at the insertion end adapted to support the stem of the intrauterine device and (ii) a handle at the posterior end, said handle being bifurcated with stems extending in an anterior or forward direction and and having flanges with edges projecting oppositely to that in the handle of the inserter tube, said flanges further being spatially opposed and abuttable with the flanges of the inserter tube handle;

wherein the lumen in the manipulative section of the tube and the coacting rod have a non-circular cross-setional configuration;

wherein the stems of one of the bifurcated handles is compressible and when compressed is adapted to be received in the area between the stems of the other handle; and wherein said tube and said rod are adaptable to coacting in a manner so that (i) pulling rearwardly on the inserter tube handle until the flanges of the stems of the inserter tube and rod handles are abutting causes a folding of the arms of the intrauterine device and moves it to the insertion position with the contoured tip and the folded arms minimally projecting from the insertion end of the tube, (ii) compressing the compressible stem of one of the handles and drawing it within the area between the stems of the other handle releases the intrauterine device at the insertion end, and (iii) releasing the compression pressure on the stem causes the inwardly and outwardly projecting edges of the handle susceptible to interlocking for a unitary withdrawal of the tube and rod from the uterus.

2. An instrument according to claim 1 wherein the compressible stems are those of the inserter tube handle and wherein the projecting edges of the fanges extend in an outward direction in the inserter tube handle and in an inward direction in the rod handle.

3. An instrument as in claim 2 wherein the handle of rod is provided with a digit placement area.

4. An instrument as in claim 1 wherein the inserter tube is provided with graduations.

5. An instrument as in claim 1 wherein the manipulative section of the inserter tube and the coacting rod are made of acrylic-butadiene-styrene plastic and the insertion section of the inserter tube and the tubular receptacle section of the rod are made of polyethylene.

6. A combination intrauterine device and instrument for inserting the same into the uterus comprising (1) a flexible intrauterine device, said device having two transverse arms distally extending from a stem;

(2) an insertion instrument comprising (a) an inserter tube adapted to protectively house said intrauterine device with the arms folded adjacent to the stem in an axially aligned position, said tube having an insertion section of a flexible nature and a manipulative section of a non-flexible nature, said tube having (i) an externally mounted slidable stop means for engaging the cervical os, said stop means being located on the insertion section of the tube, said stop means susceptible of adjustment to a pre-determined position for insertion, (ii) a pair of diametrically opposed axially extending apertures located on the manipulative section of the tube posteriorly of the stop means, said apertures adapted to receive the intrauterine device so that the stem extends axially within the tube and the arms extend through said apertures; and (iii) a handle at the posterior end of the tube, said handle being an integral part of the manipulative section and having a passageway therethrough, said passageway in communication with the lumen of the tube and further being bifurcated with the stems extending in a posterior direction and terminating in a flange with an outwardly projecting edge; and (b) a coacting rod of malleable material of retentive memory in telescopic relationship to the inserter tube and slidable therein, said rod having (i) a tubular receptacle section at the insertion end and adapted to support the stem of the intrauterine device and (ii) a handle at the posterior end, said handle being bifurcated with stems extending in an anterior or forward direction and having flanges with inwardly projecting edges, said flanges being spatially opposed and abuttable with the flanges of the inserter tube handle, and said stems further bracketing a cut out area, said cut out area being adapted to receive the compressed stems of the inserter tube handle and being at least as deep as the distance occupied by the arm of the intrauterine device within the tube when in the insertion position;

wherein the lumen in the manipulative section of the tube and the coacting rod have a non-circular cross-sectional configuration;

and wherein said tube and said rod are adaptable to coacting in a manner that (i) pulling rearwardly on the inserter tube handle until the flanges of the stems of the inserter tube and rod handles are abutting causes a folding of the arms of the intrauterine device and moves it to the insertion position with the contoured tip and the folded arms minimally projecting from the insertion end of the tube, (ii) compressing the stem of the inserter tube handle and further pulling rearwardly until the stem reaches the bottom of the cut out portion of the rod handle releases the intrauterine device at the insertion end and (iii) releasing the compression pressure causes the outwardly projecting edge of the inserter tube handle and the inwardly projecting edge of the rod handle susceptible to interlocking for unitary withdrawal of the tube and rod from the uterus.

7. A combination as in claim 6 wherein the handle of the rod is provided with a digit placement area.

8. A combination as in claim 6 wherein the inserter tube is graduated.

9. A combination as in claim 6 wherein the manipulative section of the inserter tube and the coacting rod are made of acrylic-butadiene-styrene plastic and the insertion section of the inserter tube and the tubular section of the rod are made of polyethylene.

10. A method of inserting into the uterus an intrauterine device having a stem and at least one substantially horizontal arm extending from the stem which comprises (1) providing a combination intrauterine device and insertion instrument of claim 6, (2) adjusting the stop means on the inserter tube to the desired insertion position (3) drawing backward on the inserter tube handle until the flanges of the stems of the inserter tube handle are in abutting contact with the flanges of the stems of the coacting rod handle whereupon the arms of the device are drawn backward into a folded position and the device is urged to the insertion position at the insertion end of the tube;

(4) inserting the instrument bearing the protectively mounted intrauterine device into the uterus until the stop means makes contact with the cervical os;

(5) compressing the stems of the handle of the inserter tube and drawing backward until the bottom of the cut out portion of the rod handle is reached thereby withdrawing the portion of the tube protectively housing the intrauterine device and freeing device from said tube; and (6) releasing the pressure on the stems of the inserter tube handle to place the projecting edges of the stem flanges of the handles of the inserter tube and the rod in interlocking relationship;

(7) withdrawing the instrument from the uterus.

11. A combination package to be employed for contraception consisting of
(a) a combination intrauterine device and in-insertion instrument of claim 6, and
(b) a uterine sound consisting essentially of a rod of malleable material with retentive memory and having a handle at the posterior end wherein said rod is provided with graduations and an externally mounted slidable stop means suitable for indicating the position of the cervical os;
wherein the distance indicated by the graduations on the uterine sound correspond directly with the distance readable on the graduations on the inserter tube and the shape of the sound handle correspond with the shape of the coacting rod handle of the insertion instrument.

12. An instrument for inserting into a uterus an intrauterine device including a stem and a flexible substantially transversely extending arm comprising:
an inserter tube with an axial bore therethrough and having an insertion end and a posterior end, said tube including an aperture communicating with said bore located intermediate said ends, said aperture adapted to allow receipt of the device therethrough into said bore with the arm of said device extending through said aperture; a rod slidably positioned in said bore and having a forward end adapted to receive the stem of said device and having a rearward end extending out of the posterior end of said tube, said rod adapted to slide in said bore to thereby fold said extending arm into said bore and move said device with the folded arm toward said insertion end; disengageable stop means associated with the posterior end of said tube and the rearward end of said rod adapted to stop the movement of said folded device at a pre-insertion position at said insertion end and for preventing inadvertent expulsion of said device from said tube, said stop means being disengageable by the operator of said instrument to allow said rod to slide in the direction of said insertion end to release said device from said tube and allow said folded arm to flex outwardly; and control means associated with said tube and said rod adapted to allow said rod to slide a controlled distance in the direction of said insertion end after said stop means has become disengaged so that said device is released in a controlled position in the uterus.

* * * * *

UNITED STATES PATENT AND TRADEMARK OFFICE
CERTIFICATE OF CORRECTION

PATENT NO. : 4,143,656
DATED : MARCH 13, 1979
INVENTOR(S) : GORDON WILLIAM HOLMES

It is certified that error appears in the above-identified patent and that said Letters Patent are hereby corrected as shown below:

Column 2, line 15:  "an" should read -- in --.
Column 2, line 43:  "tube of facilitate" should read -- tube to facilitate --.
Column 3, line 8:  "horizontaly" should read -- horizontally --.
Column 6, line 64:  "extendig" should read -- extending --.
Column 10, line 9:  "cervical cs" should read -- cervical os --.
Column 10, line 28:  "naturel" should read -- natural --.
Column 11, Claim 2, line 43:  "of" should read -- for --.
Column 11, Claim 2, line 43:  "fanges" should read -- flanges --.

Column 2, Line 60, "provide insertion" should be -- provide an insertion --.
Column 3, Line 33, "cervical os which is" should be cervical os. This stop is --.
Column 4, Line 22, "stem" should be -- stems --.
Column 4, Line 34, "acting as" should be -- acts as --.
Column 9, Line 29, "part" should be -- parts --.
Column 10, Line 61, "mean" should be -- means --.
Column 11, Line 14, "direction and and having" should be direction and having --.
Column 13, Line 26, "in-insertion" should be -- insertion --.

Signed and Sealed this

Fifteenth Day of January 1980

[SEAL]

Attest:

SIDNEY A. DIAMOND

Attesting Officer    Commissioner of Patents and Trademarks